United States Patent
McCauley (10) Patent No.: US 10,585,072 B2
(45) Date of Patent: Mar. 10, 2020

(54) GC COLUMN FERRULES HAVING FIRST AND SECOND DEFORMABLE SURFACES

(71) Applicant: Thermo Finnigan LLC, San Jose, CA (US)

(72) Inventor: Edward B. McCauley, Cedar Park, TX (US)

(73) Assignee: THERMO FINNIGAN LLC, San Jose, CA (US)

( * ) Notice: Subject to any disclaimer, the term of this patent is extended or adjusted under 35 U.S.C. 154(b) by 0 days.

(21) Appl. No.: 16/113,957

(22) Filed: Aug. 27, 2018

(65) Prior Publication Data

US 2018/0364204 A1    Dec. 20, 2018

Related U.S. Application Data

(63) Continuation-in-part of application No. 15/083,678, filed on Mar. 29, 2016, now Pat. No. 10,184,922.

(51) Int. Cl.
| | |
|---|---|
| *G01N 30/60* | (2006.01) |
| *B01J 20/283* | (2006.01) |
| *B01J 20/281* | (2006.01) |
| *C09D 179/08* | (2006.01) |
| *G01N 30/02* | (2006.01) |

(52) U.S. Cl.
CPC ........ *G01N 30/6078* (2013.01); *B01J 20/283* (2013.01); *C09D 179/08* (2013.01); *G01N 30/482* (2013.01); *G01N 30/6026* (2013.01); *B01J 2220/54* (2013.01); *G01N 2030/025* (2013.01)

(58) Field of Classification Search
CPC .......... G01N 30/6026; G01N 30/6034; G01N 30/6039; G01N 30/6052; G01N 30/6073; G01N 30/6078; G01N 2030/025; B01D 53/025

See application file for complete search history.

(56) References Cited

U.S. PATENT DOCUMENTS

| | | |
|---|---|---|
| 5,938,919 A | 8/1999 | Najafabadi |
| 8,128,131 B2 | 3/2012 | Barnett et al. |
| 2005/0041931 A1 | 2/2005 | Lampert |
| 2007/0000828 A1 | 1/2007 | Norman et al. |
| 2007/0003447 A1 | 1/2007 | Gleason et al. |
| 2012/0169040 A1 | 7/2012 | Barnett et al. |
| 2015/0260694 A1 | 9/2015 | Matsuoka et al. |
| 2017/0082584 A1 * | 3/2017 | Takemoto .............. G01N 30/60 |

\* cited by examiner

*Primary Examiner* — Robert Clemente
(74) *Attorney, Agent, or Firm* — David A. Schell (57) ABSTRACT

A capillary column includes a fused silica tubing, a polyimide coating over the fusing silica tubing, and a first plurality of integrated ferrules positioned along at least a first portion of the fused silica tubing and spaced apart from one another by a first fixed interval. Each of the first plurality of integrated ferrules includes a first deformable surface and a second deformable surface. The first plurality of integrated ferrules are secured to the column through deformation of the first deformable surface and the second deformable surface is configured to form a seal with a junction when secured with a nut.

22 Claims, 6 Drawing Sheets

GC COLUMN FERRULES HAVING FIRST AND SECOND DEFORMABLE SURFACES

CROSS-REFERENCE TO RELATED APPLICATIONS

The present application is a continuation-in-part under 35 U.S.C. § 120 and claims the priority benefit of co-pending U.S. patent application Ser. No. 15/083,678, filed Mar. 29, 2016. The disclosure of the foregoing application is incorporated herein by reference.

FIELD

The present disclosure generally relates to the field of gas chromatography including gas chromatography column ferrules having first and second deformable surfaces.

INTRODUCTION

Gas chromatography (GC) is used for separating and analyzing compounds that can be vaporized without decomposition. GC can be used to test the purity of a particular substance, separate the different components of a mixture, determine the relative amounts of different components of a mixture, and the like. In gas chromatography, the mobile phase (or "moving phase") is a carrier gas, usually an inert gas such as helium or an unreactive gas such as nitrogen. The stationary phase is a layer of liquid or polymer on an inert solid support, inside a column, generally a piece of glass or metal tubing.

The gaseous compounds being analyzed interact with the stationary phase coated on the inner wall of the column. Due to differences in the degree of interaction between the stationary phase and each compound, compounds can elute at a different time, known as the retention time of the compound. The retention time can be a function of the compound, the stationary phase, the carrier gas flow rate, the temperature, the length of the column, and other factors.

When a column is of insufficient length, there may be inadequate separation between compounds due to the difference in retention times being too small. However, it can periodically become necessary to trim the end of the column (particularly the end adjacent to the sample injector) due to non volatile matrix residuals that become trapped within the first few inches of the column. For example, highly polar compounds that interact so strongly with the stationary phase as to become substantially immobile can become trapped within the initial portion of the column. These trapped compounds can result in poor chromatographic peak shapes, undesirable shifts in retention times and poor quantitation of targeted compounds. Trimming the column can re-establish good chromatography, yet it presents several challenges. First, positioning the ferrule at an appropriate length to ensure the end of the column is inserted through an aperture to the right distance can require multiple measurements to position the ferrule and to confirm the ferrule has not moved during the process. Second, contamination can be introduced if a marking fluid or adhesive tape is used on the column as a visual aid for proper positioning. Third, it can be a tedious endeavor to thread the tiny bore column through a small ferrule in the relatively dark confines of a GC oven without proper eyesight, lighting, or magnification tools. Fourth, it is problematic to track the remaining length of column to correct for changes in retention time as well as to know when the column needs to be replaced due to the remaining column being too short.

From the foregoing it will be appreciated that a need exists for improvements in gas chromatography columns.

SUMMARY

In a first aspect, a capillary column can include a fused silica tubing; a polyimide coating over the fusing silica tubing; and a first plurality of integrated ferrules positioned along at least a first portion of the fused silica tubing and spaced apart from one another by a first fixed interval. Each of the first plurality of integrated ferrules can include a first deformable surface and a second deformable surface. The first plurality of integrated ferrules can be secured to the column through deformation of the first deformable surface, and the second deformable surface can be configured to form a seal with a junction when secured with a nut.

In various embodiments of the first aspect, the first fixed interval can be not less than an insertion depth.

In various embodiments of the first aspect, the first plurality of integrated ferrules can be oriented in a first direction and first portion of the fused silica tubing can be located at or near a first end of the capillary column, and can further include a second plurality of integrated ferrules positioned along a second portion of the fused silica tubing and spaced apart from one another by a second fixed interval, the second portion of the fused silica tubing can be located at or near a second end of the capillary column In particular embodiments, the first fixed interval can be greater than the second fixed interval.

In various embodiments of the first aspect, the plurality of integrated ferrules can include a metal.

In various embodiments of the first aspect, the first surface can be deformed with multiple small deformations spaced circumferentially around each of the first plurality of integrated ferrules.

In particular embodiments, the multiple small deformations can include three small deformations spaced apart from one another by about 120° or four small deformations spaced apart from one another by about 90°. In particular embodiments, the multiple small deformations can include five small deformations spaced apart from one another by not more than about 72°.

In various embodiments of the first aspect, the first surface can be deformed with annular deformation that extends substantially circumferentially around each of the first plurality of integrated ferrules. In particular embodiments, wherein the annular deformation can extend at least 75% of the circumference.

In a second aspect, a method of manufacturing a capillary column can include obtaining a polyimide coated fused silica tubing; and affixing a plurality of ferrules to the polyimide coated fused at a fixed interval from one another, the first plurality of integrated ferrules including a first deformable surface and a second deformable surface, the second deformable surface configured to form a seal with a junction when secured with a nut, wherein affixing the first plurality of integrated ferrules to the column includes deforming the first deformable surface.

In various embodiments of the second aspect, obtaining the polyimide coated fused silica tubing can include forming a fused silica tubing; and coating the fused silica tubing with one or more layers of polyimide.

In various embodiments of the second aspect, the fixed interval can be not less than an insertion depth.

In various embodiments of the second aspect, the plurality of integrated ferrules can include a metal.

In various embodiments of the second aspect, deforming the first deformable surface can include forming multiple small deformations spaced circumferentially around each of the first plurality of integrated ferrules. In particular embodiments, the multiple small deformations can include three small deformations spaced apart from one another by about 120° or four small deformations spaced apart from one another by about 90°. In particular embodiments, the multiple small deformations can include five small deformations spaced apart from one another by not more than about 72°.

In various embodiments of the second aspect, deforming the first deformable surface can include forming annular deformation that extends substantially circumferentially around each of the first plurality of integrated ferrules. In particular embodiments, the annular deformation can extend at least 75% of the circumference.

In a third aspect, a method of affixing a ferrule to a capillary column, can include obtaining a chromatography tubing, the tubing including a chromatography medium; positioning a ferrule on the chromatography tubing, the ferrule including a first deformable surface for securing the ferrule to the column and a second deformable surface for forming a seal between the column and a junction; and affixing the ferrule to the column by deforming the first deformable surface.

In various embodiments of the third aspect, the first surface can be deformed with multiple small deformations spaced circumferentially around each of the first plurality of integrated ferrules. In particular embodiments, the multiple small deformations can include three small deformations spaced apart from one another by about 120° or four small deformations spaced apart from one another by about 90°. In particular embodiments, the multiple small deformations can include five small deformations spaced apart from one another by not more than about 72°.

In various embodiments of the third aspect, the first surface can be deformed with annular deformation that extends substantially circumferentially around each of the first plurality of integrated ferrules. In particular embodiments, the annular deformation can extend at least 75% of the circumference.

DRAWINGS

For a more complete understanding of the principles disclosed herein, and the advantages thereof, reference is now made to the following descriptions taken in conjunction with the accompanying drawings, in which.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of gas chromatography columns are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Gas Chromatography Systems

Figure 1:
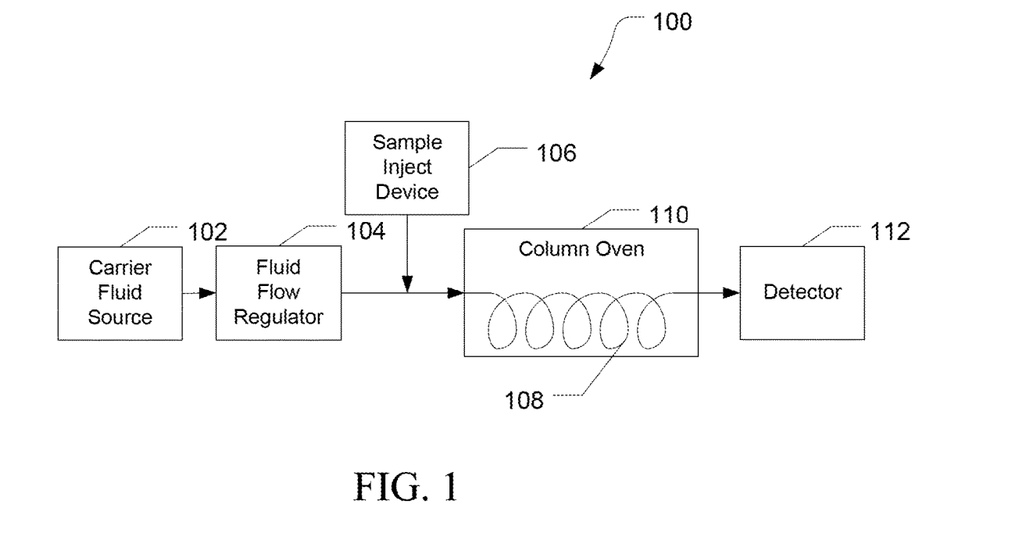
FIG. 1 is a block diagram of an exemplary gas chromatography system, in accordance with various embodiments.

Various embodiments of gas chromatography system 100 can include components as displayed in the block diagram of FIG. 1. In various embodiments, elements of FIG. 1 can be incorporated into gas chromatography system 100. According to various embodiments, gas chromatography system 100 can include a carrier fluid source 102, a fluid flow regulator 104, a sample inject device 106, a column 108, a column oven 110, and a detector 112.

In various embodiments, the carrier fluid source 102 provides a carrier fluid to the chromatography system 100. The carrier fluid can typically be a gas, such as helium, nitrogen, argon, hydrogen, air, or any combination thereof.

In various embodiments, the fluid flow regulator 104 regulates a flow of the carrier fluid through the gas chromatography system 100. The carrier gas transports a sample into and through the column 108. The carrier gas linear velocity can affect the analysis with a higher linear velocity resulting in a faster analysis, but lower separation between analytes.

Early GCs used chromatographic columns loosely packed with diatomaceous earth substrates coated with a certain percentage of stationary phase liquid. These early GC columns typically consumed 30 sccm of carrier gas or more, and were constructed of all glass tubing having a typical length of one or two meters and an internal diameter of 2 to 6 millimeters. Flow in these columns was controlled using mechanical flow controllers designed to keep a constant flow rate independent of the column back pressure. This is advantageous when employing detectors sensitive to the column effluent flow rate. When the stationary phase of these columns became contaminated with non volatile matrix deposits, it was necessary to re-pack at least the initial portion of these columns in order to re-establish chromatographic performance. It was not practical to trim these columns to remove the contaminated portion of the stationary phase, since the columns were generally all glass construction. Doing so would result in the inability to reconnect the column with injector and detector ports as well as result in significant changes in retention times and separating power. Conversely, with the introduction of wall coated open tubular fused silica capillary GC columns having much greater length, replacing the stationary phase became impractical; yet trimming the column became possible due to the inherent flexibility of fused silica and the long relative lengths of these types of columns. Trimming can be employed to restore chromatographic performance without undue loss in separation power, since capillary columns are generally tens of meters in length, while only a few tens of centimeters are required to trim such columns in order to restore performance. Mechanical flow controllers were no longer suitable on these columns due to the far lower flow rates employed. A typical open tube capillary column consumes only a few standard cubic centimeters per minute which is difficult to regulate with mechanical type flow controllers. Instead, the column flow rate is controlled indirectly using an applied pressure according to the well known Poiseuille equation.

$$\frac{dV}{dT} = \frac{\pi r^4}{16\eta L}\left(\frac{(p_i^2 - p_o^2)}{p_o}\right)$$ Equation 1 where:
$P_i$ inlet pressure
$P_o$ outlet pressure
L is the length of the column
$\eta$ is the viscosity of the gas (a function of temperature)
r is the column internal radius Modern GC's electronically control the carrier gas pressure in accordance with equation 1. Consequently, carrier pressures and flow rates can be adjusted during the run under a closed loop computer algorithm, creating pressure and or flow programs similar to temperature programs. As can be seen in equation 1, the column internal diameter as well as the column length is required for proper flow control of carrier gas in these systems. As a capillary column is routinely trimmed, the new column length needs to be entered into the control program of the chromatograph. Additionally, if a column is to be removed from a chromatograph for storage and later use, a logbook needs to be established linking the serial number of the column to its present length, since no visual aid is present which indicates the remaining length of column.

In various embodiments, the sample inject device 106 can be used to load or inject a sample into the system 100. The sample inject device 106 can be heated to vaporize the sample so it can be carried into the column 108 by the carrier gas. The sample inject device 106 can be a split/splitless injector enabling the user to choose between injecting the full concentration of sample in splitless mode (useful for small or dilute samples) or dilute the sample with the carrier gas in split mode (useful for concentrated samples).

In various embodiments, the column 108 is generally a fused silica or metallic capillary column with a stationary compound coating the inner surface. Common stationary phases in open tubular columns are cyanopropylphenyl, dimethyl polysiloxane, carbowax (polyethyleneglycol), bis-cyanopropyl, cyanopropylphenyl polysiloxane and diphenyl dimethyl polysiloxane.

In various embodiments, the column oven 110 can control the temperature of the column 108. The temperature of oven 110 can be precisely controlled electronically.

The rate at which a sample passes through the column can be directly proportional to the temperature of the column. The higher the column temperature, the faster the sample can move through the column. However, the faster a sample moves through the column, the less time it has to interact with the stationary phase, resulting in less separation between components of the sample. In general, the column temperature is often selected as a compromise between the length of the analysis and the degree of separation.

In various embodiments, the temperature may be held constant throughout the analysis (isothermal separation). In other embodiments, the temperature can be varied (generally increasing) throughout the run. By controlling and adjusting the initial temperature and the rate of increase, adequate separation can be achieved for certain compounds while decreasing the overall run time by sacrificing separation in other parts of the run.

In various embodiments, the detector 112 can detect components of the sample as they exit the column, and correlate the measurement with a retention time. Numerous detectors can be incorporated, including flame ionization detectors (FID), thermal conductivity detectors (TCD), catalytic combustion detectors (CCD), discharge ionization detectors (DID), electron capture detectors (ECD), flame photometric detectors (FPD), Infrared detectors (IRD), mass spectrometers (MS), vacuum ultraviolet detectors (VUV), and the like.

Figure 2:
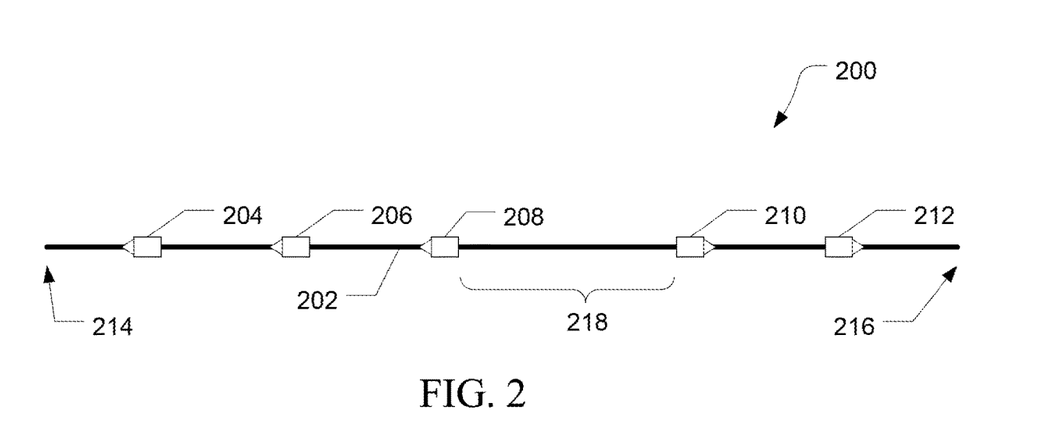
FIG. 2 is a schematic diagram of an exemplary gas chromatography column with integrated ferrules, in accordance with various embodiments.

FIG. 2 is a diagram 200 depicting a GC column 202 with integrated ferrules 204, 206, 208, 210, and 212. Column 202 can be a fused silica column with a polymer coating on the outer surface of the column. In various embodiments, the polymer coating can be a polyimide coating. Alternatively, column 202 can be a metal column or a metal clad column.

The inner surface of the column can include a stationary phase appropriate for GC separation of compounds.

Column 202 can include an end 214 and an end 216. Integrated ferrules 204, 206 and 208 can be located near end 214 and oriented to be used in conjunction with end 214. Integrated ferrules 210 and 212 can be located near end 216 and be oriented to be used in conjunction with end 216. For example, end 214 can be coupled to an injection port of the GC system, such as GC system 100, and end 216 can be coupled to a detector. In various embodiments, end 214 or end 216 can be inserted through an orifice with an insertion length of column extending through the orifice and a ferrule and nut used to secure the column in place and prevent leaks.

In various embodiments, integrated ferrules 204, 206, 208, 210, and 212 can include graphite, a polymer such as polyimide, or a combination thereof. Alternatively, the integrated ferrules 204, 206, 208, 210, and 212 can be formed of metal.

In various embodiments, the integrated ferrules 204, 206, 208, 210, and 212 can be fixed to the column by cementing with a polymer bonding agent, such as using a polyimide glue to adhere the integrated ferrules 204, 206, 208, 210, and 212 with a polyimide coating on column 202. In alternate embodiments, the ferrules can be pre-swaged to the column to prevent slippage.

Integrated ferrules 204, 206, and 208 can be fixed to the GC column at fixed intervals. In various embodiments, the fixed interval can be not less than the insertion depth of the column, such as when inserted into injection port. The insertion depth can be the depth necessary to insert the column through an orifice of the GC system to ensure proper leak free connectivity between the column and another component of the GC system, such as the injection port.

In various embodiments, integrated ferrules 210 and 212 can be oriented in an opposite direction than integrated ferrules 204, 206, and 208. For example, integrated ferrules can be oriented to be used in conjunction with the detector. Further, integrated ferrules 210 and 212 can be spaced apart by a fixed interval different than, such as greater than, the fixed interval used in spacing integrated ferrules 204, 206, and 208, such as when the insertion depth for coupling with the detector is different than the insertion depth for coupling with the injection port. Further, as the injection port side of the column may be more frequently trimmed than the detector side of the column, more integrated ferrules may be oriented for use with end 214.

In various embodiments, the column may include a gap 218 separating the first group of ferrules oriented in a first direction (integrated ferrules 204, 206, and 208) from the second group of ferrules orient in the second direction (integrated ferrules 210 and 212). After the last ferrule on one side of the column is used (such as ferrule 208), the column may need replacement. The length of gap may be a minimum useful column length, such that using a shorter column would result in insufficient resolution of compounds.

Figure 3A:
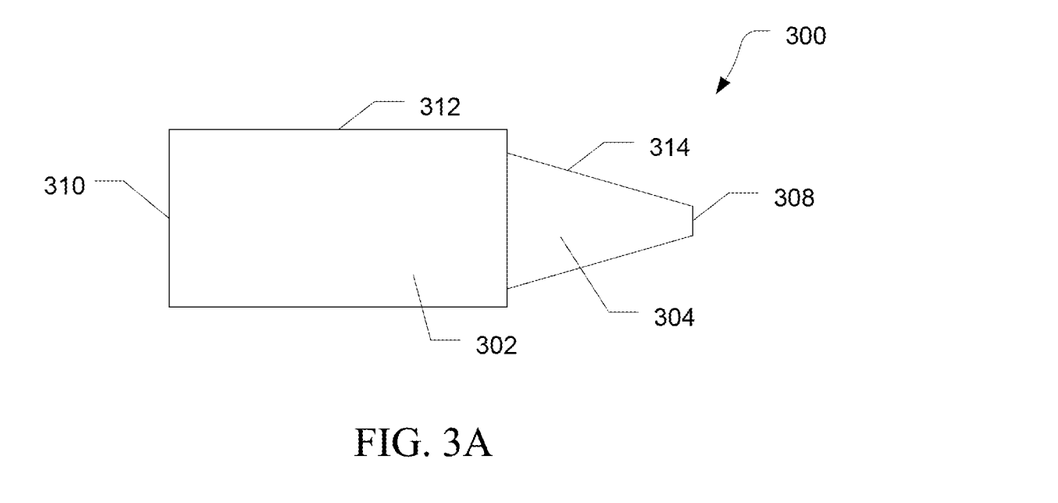
FIGS. 3A and 3B are schematic diagrams illustrating an exemplary ferrule, in accordance with various embodiments.
Figure 3B:
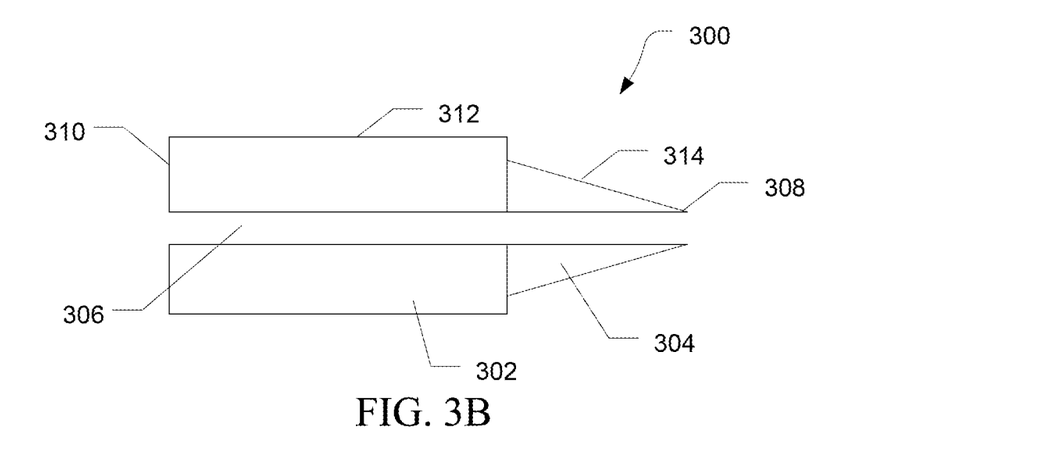
Figure 4A:
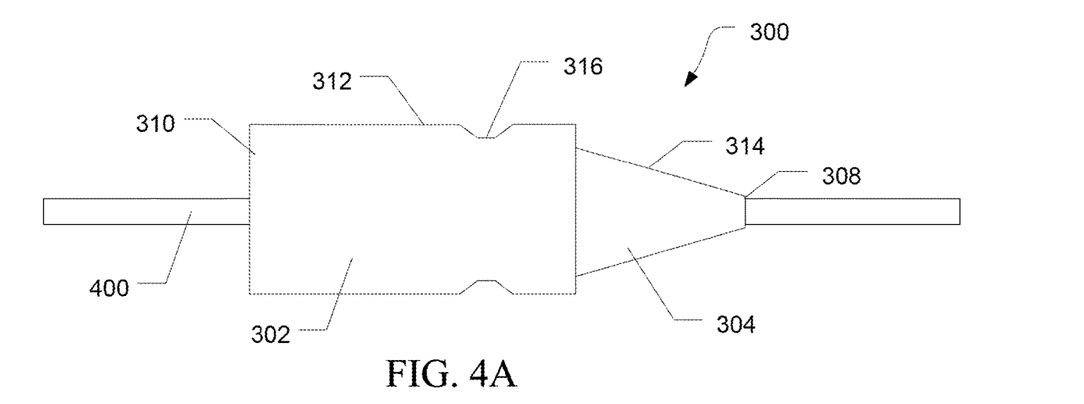
FIGS. 4A and 4B are schematic diagrams illustrating an exemplary ferrule secured to a gas chromatography column, in accordance with various embodiments.
Figure 4B:
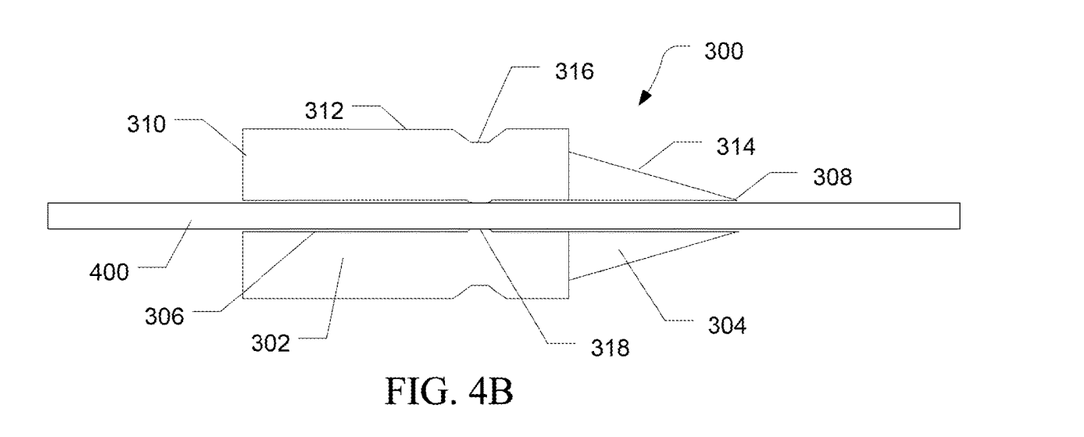

FIGS. 3A and 3B illustrate an exemplary ferrule 300. FIG. 3B is a cross section of ferrule 300. Ferrule 300 includes a first portion 302 and a conical second portion 304 and a channel 306 extending from a proximal end 308 of the second portion 304 to a distal end 310 of the first portion 302. The first portion 302 can include a first deformable surface 312. The second portion 304 can include a second deformable surface 314. Deformation of the first deformable surface 312 can be used to secure the ferrule 300 to a gas chromatography column, as illustrated in FIGS. 4A and 4B. Deformation of the second deformable surface 314 of the conical second portion can be used to secure and seal the column to a union, such as at an inlet or outlet of the column.

FIGS. 4A and 4B illustrate ferrule 300 secured to a gas chromatography column 400. FIG. 4B is a cross section of ferrule 300 and column 400. Column 400 fits through channel 306. A crimp 316 in the first deformable surface 312 causes an interior deformation 318 that secures the column 400 in place. In various embodiments, the crimp 316 can include multiple small crimps spaced around the circumference of the ferrule 300, such as two small crimps opposite one another, three small crimps spaced about 120° from one another, four small crimps spaced about 90° from one another, or five or more small crimps spaced no more than about 72° from one another. In other embodiments, more crimps can be used. In yet another embodiment, an annular crimp can be used that substantially extends around the circumference of the ferrule 300, such as at least 75% of the circumference, at least 85% of the circumference, even at least 95% of the circumference.

In various embodiments, the deformation of the first deformable surface 312 can be performed without deforming the second deformable surface 314. Deforming the second deformable surface 314 prior to connecting the column 400 to a fitting can result in small leaks at the junction, such as between the column and the ferrule or between the ferrule and the junction. Significantly, these small leaks can introduce detectable amounts of air and water vapor into a mass spectrometer detector and affect the performance and sensitivity of the mass spectrometer detector.

Figure 5A:
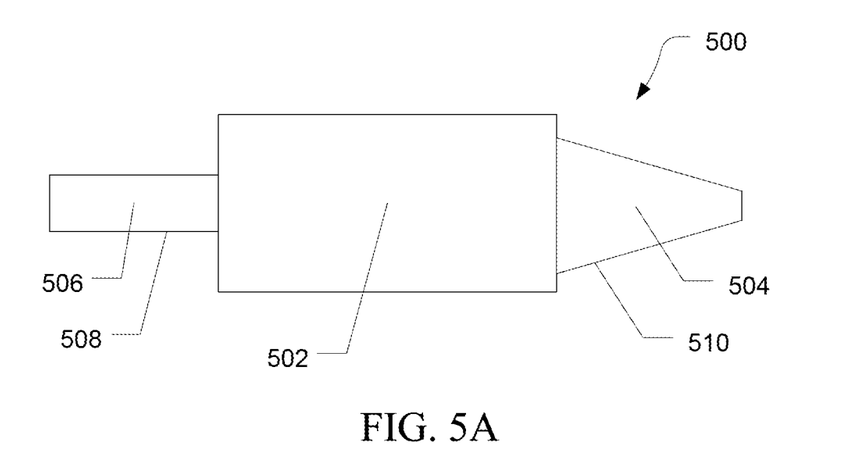
FIGS. 5A and 5B are schematic diagrams illustrating additionally exemplary ferrules, in accordance with various embodiments.

FIGS. 5A and 5B illustrate alternate embodiments of ferrules. Ferrule 500 shown in FIG. 5A includes a body portion 502, a conical portion 504, and an extension portion 506. The extension portion 506 can include a first deformable surface 508 and the conical portion 504 can include a second deformable surface 510. As with ferrule 300 of FIG. 3A, deformation of the second deformable surface 510 of the conical portion 504 can be used to form a seal between the column with a fitting or junction. Ferrule 500 can be secured to a column by deforming the first deformable surface 508 of extension portion 506, deforming the body portion 502, or a combination thereof.

Figure 5B:
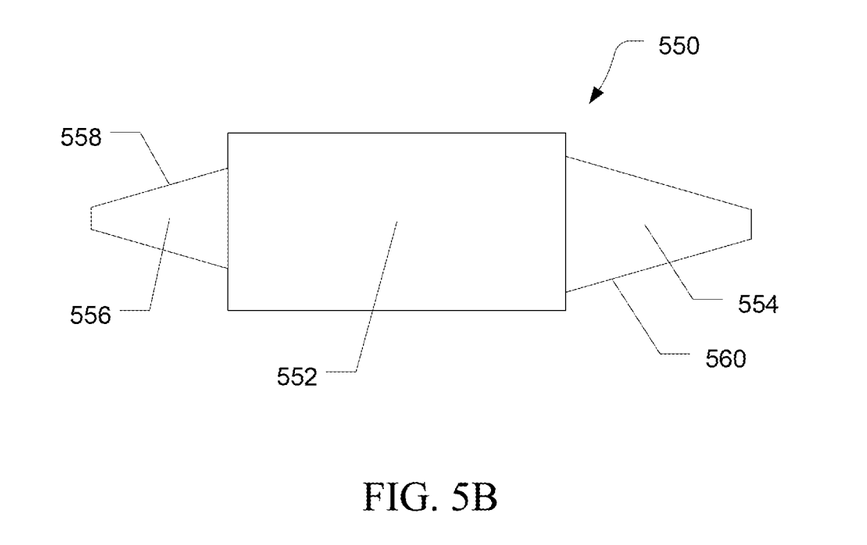

Ferrule 550 shown in FIG. 5B includes a body portion 552, a conical portion 554, and a conical extension portion 556. The extension portion 556 can include a first deformable surface 558 and the conical portion 554 can include a second deformable surface 560. As with ferrule 300 of FIG. 3A, deformation of the second deformable surface 560 of the conical portion 554 can be used to form a seal between the column and a fitting or junction. Ferrule 550 can be secured to a column by deforming the first deformable surface 558 of the conical extension portion 556, deforming body portion 552, or a combination thereof.

Figure 6:
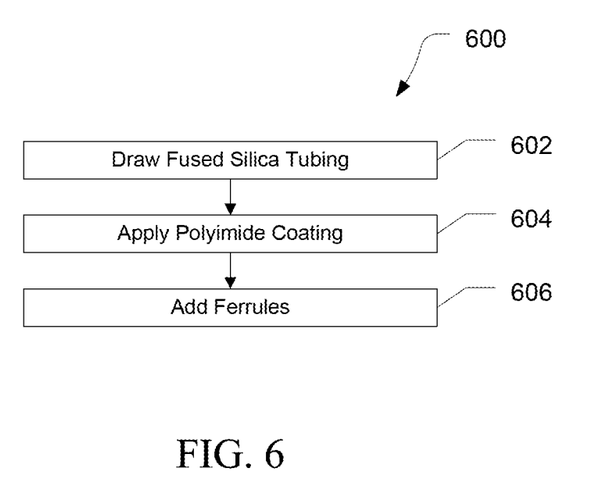
FIG. 6 is a flow diagram illustrating a method of making a gas chromatography column with integrated ferrules, in accordance with various embodiments.

FIG. 6 is a flow diagram of a method of manufacturing a column with integrated ferrules. At 602, fused silica tubing can be drawn. In various embodiments, the tubing can be continuously pulled from molten silicon dioxide, typically from a high purity fused silica pre-form. As the tubing is pulled, it can be appropriately sized, such as by controlling the inner diameter, the outer diameter, the wall thickness, or any combination thereof, and cooled to hold the size and shape.

At 604, the fused silica tubing can be coated in one or more layers of a polymer, such as polyimide. In various embodiments, the tubing can be dipped in the polymer one or more times with the polymer being allowed to polymerize or cool between dips. In particular embodiments, the tubing can be formed continuously. A continuous tube can be drawn from the molten silicon dioxide, guided through a controlled cooling/annealing zone, and through the polymer bath. The tubing may loop through a polymerizing/cooling zone and back into the polymer bath a plurality of times to provide sufficient thickness of the polymer coating.

At 606, ferrules can be added to the tubing at predetermined locations along the tubing. In various embodiments, the ferrules can include graphite, a polymer such as polyimide, or a combination thereof. Alternatively, the ferrules can be metal. The ferrules can be positioned such that they are spaced apart by a fixed interval, such as a length not less than the insertion depth necessary when the column is in use.

In various embodiments, the tubing may be cut to size and then the ferrules threaded onto the tubing and positioned before affixing the ferrules to the tubing. In various embodiments, the ferrules can be affixed by pre-swaging. In other embodiments, the ferrules can be affixed using a polymer bonding agent to bond the ferrules to the polymer coating. In yet other embodiments, the ferrules may be formed in place on the tubing, such as by molding or casting in place. In particular embodiments, the ferrules can be formed on the continuously forming tubing, such as by a two part mold coming together around the moving tubing at a beginning of a ferrule forming zone. The ferrule material can be applied within the mold, and the mold can travel with the tubing through a ferrule forming zone while the ferrule is formed. The two part mold may then be removed at the end of the ferrule forming zone to reveal an integrated ferrule and then the mold can return to the beginning of the ferrule forming zone to be reused.

Figure 7:
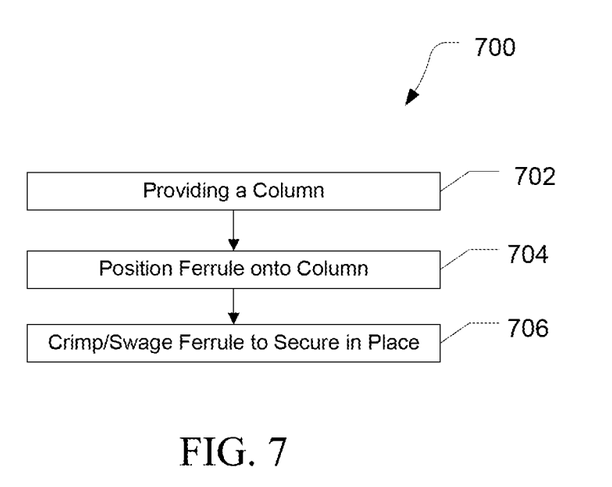
FIG. 7 is a flow diagram illustrating a method of securing a ferrule to a gas chromatography column, in accordance with various embodiments.

FIG. 7 is a flow diagram of a method of securing a ferrule to a column. At 702, a tubing can be provided. In various embodiments, the tubing can be a fused silica tubing coated in a polymer, such as polyimide, a metal clad fused silica tubing, or a metal tubing. In various embodiments, the metal clad fused silica tubing may or may not include a polymer layer between the fused silica and the metal cladding.

At 704, a ferrule, such as a metal ferrule, can be positioned on the tubing at a predetermined location. In various embodiments, the ferrule can include a first deformable surface for affixing to the column and a second deformable surface for forming a seal between the column and a junction, such as described in FIG. 3A. In various embodiments, one or more ferrules may be threaded onto the tubing and positioned before affixing the ferrules to the tubing.

At 706, the ferrule can be affixed by pre-swaging or crimping to deform the first deformable surface without deforming the second deformable surface.

Figure 8:
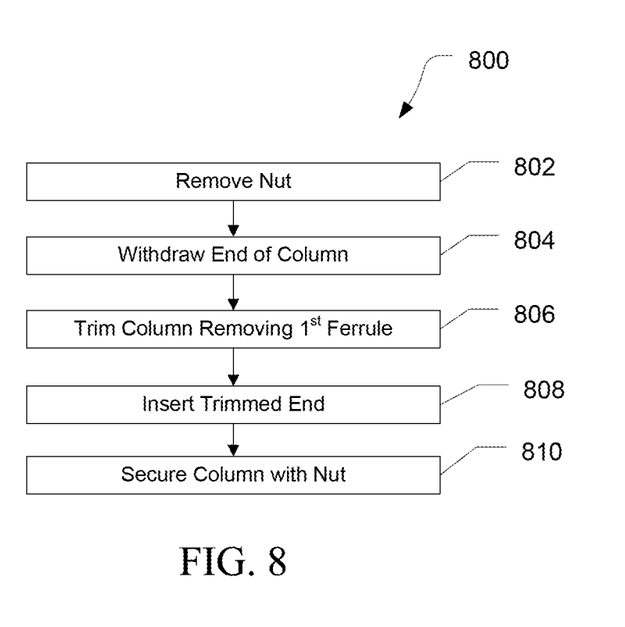
FIG. 8 is a flow diagram illustrating a method of using a gas chromatography column with integrated ferrules, in accordance with various embodiments.

FIG. 8 is a flow diagram of a method of using a column with integrated ferrules. The ferrules can include graphite, a polymer such as polyimide, or a combination thereof. Alternatively, the ferrules can be metal. The ferrules can be positioned such that they are spaced apart by a fixed interval, such as a length not less than the insertion depth necessary when the column is in use. The integrated ferrules can be affixed to the column, such as by cementing or pre-swaging.

At 802, a nut securing the column at a first ferrule can be loosened to free a first ferrule. In various embodiments, the nut can be a split nut, such that a slot on the side can be used for placing the nut around the tubing and removing the nut from the tubing to enable positioning adjacent to an appropriate integrated ferrule. In particular, after loosening the nut, the nut can be removed from the column and saved for later use.

At 804, an end of the column can be withdrawn from an orifice, and at 806, a portion of the column containing the first ferrule can be trimmed from the column. In various embodiments, the column can be trimmed to leave a length of column corresponding to an insertion depth between the new end and a second ferrule.

At 808, the new end of the column can be inserted into the orifice, up to the insertion depth, and at 810, the nut can be placed around the column and used to secure the ferrule and column within the orifice.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A capillary column comprising:
    a fused silica tubing;
    a polyimide coating over the fused silica tubing;
    a first plurality of integrated ferrules positioned along at least a first portion of the fused silica tubing and spaced apart from one another by a first fixed interval, each of the first plurality of integrated ferrules including a first deformable surface and a second deformable surface, the first plurality of integrated ferrules secured to the column through deformation of the first deformable surface, the second deformable surface configured to form a seal with a junction when secured with a nut, the first plurality of integrated ferrules are oriented in a first direction and first portion of the fused silica tubing is located at or near a first end of the capillary column; and
    a second plurality of integrated ferrules positioned along a second portion of the fused silica tubing and spaced apart from one another by a second fixed interval, the second portion of the fused silica tubing located at or near a second end of the capillary column.

2. The capillary column of claim 1 wherein the first fixed interval is not less than an insertion depth.

3. The capillary column of claim 1 wherein the first fixed interval is greater than the second fixed interval.

4. The capillary column of claim 1 wherein the plurality of integrated ferrules include a metal.

5. The capillary column of claim 1 wherein the first surface is deformed with annular deformation that extends substantially circumferentially around each of the first plurality of integrated ferrules.

6. The capillary column of claim 5 wherein the annular deformation extends at least 75% of the circumference.

7. A capillary column comprising:
    a fused silica tubing;
    a polyimide coating over the fused silica tubing; and a first plurality of integrated ferrules positioned along at least a first portion of the fused silica tubing and spaced apart from one another by a first fixed interval, each of the first plurality of integrated ferrules including a first deformable surface and a second deformable surface, the first plurality of integrated ferrules secured to the column through multiple small deformations of the first deformable surface spaced circumferentially around each of the first plurality of integrated ferrules the second deformable surface configured to form a seal with a junction when secured with a nut.

8. The capillary column of claim 7 wherein the multiple small deformations include three small deformations spaced apart from one another by about 120° or four small deformations spaced apart from one another by about 90°.

9. The capillary column of claim 7 wherein the multiple small deformations include five small deformations spaced apart from one another by not more than about 72°.

10. A method of manufacturing a capillary column, comprising:
   obtaining a polyimide coated fused silica tubing; and
   affixing a plurality of ferrules to the polyimide coated fused silica tubing at a fixed interval from one another, the plurality of integrated ferrules including a first deformable surface and a second deformable surface, the second deformable surface configured to form a seal with a junction when secured with a nut,
   wherein affixing the plurality of integrated ferrules to the column includes deforming the first deformable surface with multiple small deformations spaced circumferentially around each of the plurality of integrated ferrules.

11. The method of claim 10 wherein obtaining the polyimide coated fused silica tubing includes:
   forming a fused silica tubing; and
   coating the fused silica tubing with one or more layers of polyimide.

12. The method of claim 10 wherein the fixed interval is not less than an insertion depth.

13. The method of claim 10 wherein the plurality of integrated ferrules include a metal.

14. The method of claim 10 wherein the multiple small deformations include three small deformations spaced apart from one another by about 120° or four small deformations spaced apart from one another by about 90°.

15. The method of claim 10 wherein the multiple small deformations include five small deformations spaced apart from one another by not more than about 72°.

16. The method of claim 10 wherein deforming the first deformable surface includes forming annular deformation that extends substantially circumferentially around each of the plurality of integrated ferrules.

17. The method of claim 16 wherein the annular deformation extends at least 75% of the circumference.

18. A method of affixing a ferrule to a capillary column, comprising:
   obtaining a chromatography tubing, the tubing including a chromatography medium;
   positioning a ferrule on the chromatography tubing, the ferrule including a first deformable surface for securing the ferrule to the column and a second deformable surface for forming a seal between the column and a junction; and
   affixing the ferrule to the column by deforming the first deformable surface with multiple small deformations spaced circumferentially around the ferrule.

19. The method of claim 18 wherein the multiple small deformations include three small deformations spaced apart from one another by about 120° or four small deformations spaced apart from one another by about 90°.

20. The method of claim 18 wherein the multiple small deformations include five small deformations spaced apart from one another by not more than about 72°.

21. The method of claim 18 wherein the first surface is deformed with annular deformation that extends substantially circumferentially around each of the first plurality of integrated ferrules.

22. The method of claim 21 wherein the annular deformation extends at least 75% of the circumference.

* * * * *